United States Patent [19]

Kortright

[11] Patent Number: 4,743,543

[45] Date of Patent: * May 10, 1988

[54] METHOD FOR ENHANCING AND/OR ACCELERATING IMMUNOASSAY DETECTION OF HUMAN CARCINOMA TUMOR ASSOCIATED ANTIGEN IN A PATHOLOGY SAMPLE

[75] Inventor: Kenneth H. Kortright, Cooper City, Fla.

[73] Assignee: Coulter Corporation, Hialeah, Fla.

[*] Notice: The portion of the term of this patent subsequent to Nov. 24, 2004 has been disclaimed.

[21] Appl. No.: 774,070

[22] Filed: Sep. 9, 1985

[51] Int. Cl.$^4$ .................. G01N 33/53; G01N 33/566; G01N 33/577

[52] U.S. Cl. .......................................... 435/7; 435/29; 435/68; 435/172.2; 435/810; 435/948; 435/240.2; 436/501; 436/513; 436/519; 436/548; 436/813; 436/823; 436/825; 530/387; 424/85; 424/88

[58] Field of Search .................. 435/7, 4, 29, 68, 264, 435/172.2, 267, 272, 810, 18, 274, 240, 948, 810; 436/548, 813, 808, 501, 519, 823, 825; 424/3, 7.1, 85, 88; 530/385

[56] References Cited

U.S. PATENT DOCUMENTS 4,116,777  9/1978  Takátsy et al. ...................... 435/18
4,446,122  5/1984  Chu et al. ............................ 436/516
4,507,391  3/1985  Pukel et al. ......................... 436/520

OTHER PUBLICATIONS

Biological Abstracts, vol. 62, 1973, Abstract No. 53599, Weiss.
Biological Abstracts, vol. 69, 1979, Abstract No. 38400, Niinobe et al.
Biological Abstracts, vol. 76, 1982, Abstract No. 11845, Miyamoto et al.
Chemical Abstracts, vol. 79, 1973, Abstract No. 63073c, Kendal et al.

Primary Examiner—Robert J. Warden
Assistant Examiner—Florina B. Hoffer
Attorney, Agent, or Firm—Myron C. Cass

[57] ABSTRACT

Detection of an identified human carcinoma tumor antigen in a pathological sample by means of a labelled monoclonal antibody specific to the determinant site on the antigen is enhanced and/or accelerated at an earlier development stage than heretofore achieved by removing a carbohydrate steric hindrance for monoclonal antibody availability to bind the antigen of the tumor for which it is specific. The carbohydrate steric hindrance for monoclonal binding to the antigen is identified as sialic acid. The method of the invention involves selective removal of sialic acid from the antigen's determinant site by enzymatic digestion using neuraminidase.

5 Claims, No Drawings

METHOD FOR ENHANCING AND/OR ACCELERATING IMMUNOASSAY DETECTION OF HUMAN CARCINOMA TUMOR ASSOCIATED ANTIGEN IN A PATHOLOGY SAMPLE

RELATED APPLICATION

This patent application is related in subject matter to the pending application, Ser. No. 702,059 filed Feb. 15, 1985 titled MONOCLONAL ANTIBODY TO A HUMAN CARCINOMA TUMOR ASSOCIATED ANTIGEN and is owned by the same assignee as this patent application. The subject matter of said patent application is incorporated herein by specific reference.

BACKGROUND OF THE INVENTION

This invention relates generally to immunoassay detection of human carcinoma tumors by means of a labelled murine monoclonal antibody demonstrating reactivity to a specific antigen on the surface of human carcinoma cells and tissues, and more particularly, to a unique immunoassay method involving removal of a carbohydrate steric hindrance for such monoclonal antibody availability to bind the antigen for which it is specific.

The total immune system of a human includes an adaptive immune system whose function is to produce a specific reaction to an infectious disease which will enable recovery from the disease. In this function, the adaptive immune system is called upon to evolve molecules called antibodies. Antibodies are molecules produced by B lymphocytes having antigen binding portions which can recognize a determinant or antigenic site of the infectious disease or on diseased cells. A particular antibody molecule can bind only to one type of infectious disease or diseased cell or tissue. Further, each antibody molecule binds to only one of the many molecules on the disease microorganism's or diseased cell's surface. Those molecules to which antibodies bind are known as antigens.

It is known that different antibodies will bind to different antigens with each antibody being specific for a particular antigen. Any particular antigen molecule can have several different determinant sites or epitopes or may have several identical epitopes. Thus, antibodies really are specific for the epitopes or determinant antigenic sites rather than the whole antigen molecule. Thus, each antibody molecule effectively recognizes one epitope rather than the whole antigen.

In said related patent application, there is identified a murine monoclonal antibody which is specific for a unique antigenic determinant or epitope of a human carcinoma tumor cell. The antigen was called the "KC-4 antigen" and the monoclonal antibody was called "KC-4". The antigen molecule was isolated and identified as having two forms. The larger form has an approximate molecular weight of 490,000 daltons (range of 480,000 to 510,000), and occurs only in the cytoplasm of the carcinoma cells. The smaller form has an approximate molecular weight of 438,000 daltons (range of 390,000 to 450,000) and occurs both in the cytoplasm and membrane of carcinoma cells. A sample of both hybrid cell lines capable of producing monoclonal antibodies specific for this antigen are on deposit with the American Type Culture collection and are assigned the Nos. HB 8907 (IgG3) and HB 8710 (IgM).

This KC-4 monoclonal antibody is available commercially from the Coulter Immunology Division of Coulter Corporation, Hialeah, Flordia in a solid tumor marker kit under the registered trademark COULTER CLONE ®. This is a carcinoma marker immunoperoxidase kit which is complete for routine use with tissues such as breast, lung, prostate, stomach and colon in the investigation of adenocarcinoma and squamous cell carcinoma. The kit can be applied to single cell suspensions (cell lines), frozen sections and paraffin embedded tissues. The immunoassay kit is available for research use to identify solid tumor markers in neoplastic tissue. The KC-4 monoclonal antibody has been available for diagnostic detection of carcinoma markers by researchers using other immunoassay techniques, including flow cytometric techniques or where the KC-4 monoclonal antibody is coated on a substrate or support member such as a microsphere for binding to KC-4 antigen.

Thus, achieving meaningful diagnostic detection of the KC-4 antigen in a pathological cell sample using routine or conventional immunoassay techniques is known. Said related patent application describes numerous immunoassay techniques for detecting the binding of the KC-4 monoclonal antibody to the KC-4 antigen on the membrane or surface of a pathological sample. In each case, the reactive binding of a stained or labelled KC-4 monoclonal antibody to the determinant site or epitope of the antigen will signal its detection. Obviously critical to such detection procedures in a pathological sample is adequate monoclonal antibody availability to bind the determinant site of the antigen for which it is specific. This presumes that the antigenic determinant is freely available without hindrance to binding with its specific monoclonal antibody at all stages of development of the human carcinoma cells, including in the very early stages of carcinoma cell development. Thus, percentage of positive carcinoma cell detection is important. Also important is being able to detect such cancer at its very early development stage where the percentage of positive antigen detection may be quite small.

I have determined that there is a carbohydrate steric hindrance to binding of the KC-4 monoclonal antibody to the smaller form of KC-4 antigen on the surface or membrane of the carcinoma cell by reason of sialic acid residue on the KC-4 antigen. The expression of the KC-4 antigen on the surface of the carcinoma cell was found to be directly related to the sialic acid on the KC-4 antigen. By removal of the sialic acid on the KC-4 antigen of the tumor cell, I have been able to enhance and/or accelerate detection, as by staining or labelling of the KC-4 antigen, which was not detectable by conventional or routine in vitro immunoassay techniques. By removing the determined carbohydrate steric hindrance on the identified KC-4 antigen, I have been able to increase the ability to detect human carcinoma tumors in a pathology sample by at least a factor of two (2). The method of the invention enhances the percentage of pathological cells detectable and even provides for earlier detection of solid tumor cells than heretofore achieved by routine immunoassay techniques.

SUMMARY OF THE INVENTION

A pathology sample of the human carcinoma tumor cells is prepared either for flow cytometer or microscopic analysis. The sample tissue can be frozen or fixed, such as to be paraffin embedded. Also, fresh tissue sample can be used. The sample is selectively treated initially to digest sialic acid residue on the KC-4 antigen using the enzyme neuraminidase. An in vitro immunoassay then is conducted using the monoclonal antibody specific for the determinant side of the antigen, to wit, KC-4 monoclonal antibody suitably labelled or stained. The immunoassay is completed to ascertain the percentage of positive antigenic determinations realized.

PREFERRED EMBODIMENT OF THE INVENTION

As explained herein, the method embodying the invention is directed to enhancing and/or accelerating the percentage of positive carcinoma cell detection in a pathological sample. Multiple tests were conducted employing the invention method as explained hereinafter.

Individual frozen sections of lung carcinoma tissue and breast carcinoma tissue were tested. Also, frozen sections of normal lung and breast tissue were tested. The monoclonal antibody KC-4 was used at a selected dilution. Pathology sample were prepared for microscopic analysis to enable labelling or staining with KC-4 antibody on one set of samples slides in a routine or conventional manner and on a second set of sample slides using the method of this invention. A third set of slides was prepared to provide normal tissue in the testing procedures. A plurality of the different sets of pathology samples and normal tissue samples were prepared so as to enable testing under varying conditions as explained herein.

The sets of pathology and normal tissue sample slides initially were treated with the labelled KC-4 monoclonal antibody. Then, the second set of slides was treated with a wash of the enzyme neuraminidase. Then, the sets of slide samples were selectively incubated for thirty to sixty minute periods at a temperature of approximately 37° Celsius. Thus, the different slide sample sets were incubated for different periods of time with results monitored for each of the slide sample sets at the different incubation periods established.

The results of these test procedures were as follows:

1. No staining activity was discerned in any of the slide sample sets using normal tissue. The KC-4 monoclonal antibody did not bind to normal tissue.

2. The slide sample sets subjected to enzyme digestion using neuraminidase exhibited brighter stain discernment and a greater percentage of positive cell staining than the slide sample set which was not treated with neuraminidase.

3. Subjecting the neuraminidase treated slide sample sets to longer incubation periods revealed increased staining of the neoplastic tissue. There was an indication of some destruction of tissue architecture at the longer incubation periods.

4. Incubation at room temperature appeared preferable.

Tests were repeated using immunoperoxidase staining with KC-4 monoclonal anbibody and tissue sections of colon cancer, liver cancer, prostate cancer, breast cancer, lung cancer, both frozen and paraffin fixed. Slide sample sets were treated with neuraminidase and incubated as previously described along with sample slide sets which did not undergo neurominidase enzyme digestion. The results established that neuraminidase treated pathology samples, both frozen and paraffin fixed, stained darker than routinely treated cancer samples. This indicated a greater percentage of positive cancer detection using our neuraminidase treatment.

A further series of tests were conducted in which lung and liver sample cancer tissues were treated with neuraminidase and corresponding tissue samples were treated routinely, i.e., without neuraminidase. The KC-4 monoclonal antibody was used in each instance and a suitable incubation period at proper temperature was run with the following results:

1. In the case of the lung tissue sample treated with neuraminidase, the staining color was deeper and the percentage of positive cells detected was 37%. In the case of the non-neuraminidase treated sample, the percentage of positive cells detected was 19%.

2. In the case of liver tissue samples, the neuraminidase treated sample evidenced dark brown staining in the majority of large cells which were granular in appearance. The non-neuraminidase treated liver tissue samples evidenced only faint staining in some larger cells which appeared granular also.

I believe that the phenomena described herein bears a direct relationship to the structural and functional nature of the proteins forming the membrane of the tumor cell. Glycoproteins are integral components of cell membranes. In the case of carcinoma tumor cells, such glycoproteins have a transmembrane region on the surface of the membrane to which sugar residues, such as sialic acid, can attach. We believe that sialic acid molecules attach to the KC-4 antigen exposed on the membrane of human carcinoma tumor cells so as to mask this determinant site and prevent its being recognized by the KC-4 monoclonal antibody which does not bind to normal tissue. This is asserted because the carbohydrate sialic acid is known to be located on the exterior of a cell membrane only. When this carbohydrate is enzyme digested by neuraminidase, the KC-4 antigen becomes available for binding to the KC-monoclonal antibody and is detected more prominently as established by the test results recited.

We have provided a method for immunoassay of human carcinoma solid tumors which significantly increases location and determination of positive human carcinoma cells. By removing this sialic acid steric hindrance to availability of the KC-4 monoclonal antibody to bind to the KC-4 antigen, such cancers can be detected earlier and/or more positively than by previous immunoassay techniques in which neuraminidase was not used. The neuraminidase digests the carbohydrate, sialic acid, that appears to mask the KC-4 antigenic site and permits accelerated and/or enhanced detection of the human carcinoma tumor cells. I have increased in a most productive and useful manner the ability to detect carcinoma tumor; also I have increased the sensitivity to earlier detection of such cancer by removing the carbohydrate steric hindrance of sialic acid on the KC-4 antigen by neuraminidase treatment as described herein.

Although the method embodying the invention has been described in connection with immunoassay techniques involving slide staining of pathological samples, the method is effective and productive using other techniques such as flow cytometry and microspheres, for instance.

I claim:

1. An immunoassay method for detecting a human carcinoma associated antigen in a pathology sample of cells, comprising:

A. treating the sample of human carcinoma cells prepared for assay with neuraminidase to digest a carbohydrate residue affixed to an antigenic site on the membrane of the cell of the sample, thereby exposing antigen sites to monoclonal antibody binding;

B. contacting said cells with labelled monoclonal antibody which will bind specifically to said antigen sites to produce detectable labelled complexes at varying stages of carcinoma development; and C. assaying said sample for detecting the presence of labelled complexes, wherein the antigen of said site is identified as KC-4 antigen and the monoclonal antibody is IgG3 isotype or IgM isotype derived from the hybrid murine cell lines having American Type Culture Collection Nos. HB 8709 or HB 8710, respectively.

2. The method of claim 1 in which the carbohydrate is sialic acid and the treatment includes incubating the samples over a selected period of time at a selected temperature sufficient for the neuraminidase to digest the sialic acid and expose said antigenic sites to detectable monoclonal antibody binding thereto.

3. The method of claim 2 in which incubation treatment is performed over a period of from thirty (30) to sixty (60) minutes.

4. The method claim 3 in which the incubation treatment is performed at approximately 37° Celsius.

5. An immunoassay testing kit for carcinoma marking of neoplastic tissue to locate and identify solid tumor cells involving breast, colon, lung, stomach and prostate, said kit including:

A. a contained quantity of monoclonal antibody which binds specifically to the antigen KC-4 sited on the membranes of the cells, which antibody is IgG3 isotype or IgM isotype derived from the hybrid murine cell lines having American Type Culture Collection Nos. HB 8709 or HB 8710, respectively;

B. a contained quantity of a reagent label for the monoclonal antibody; and

C. a contained quantity of neuraminidase for application to said tissue for digesting a sialic acid residue attached to the KC-4 antigen which otherwise hinders availability of the anti-KC-4 monoclonal antibody to bind to the KC-4 antigen.

* * * * *

UNITED STATES PATENT AND TRADEMARK OFFICE
CERTIFICATE OF CORRECTION

PATENT NO. : 4,743,543
DATED : May 10, 1988
INVENTOR(S) : Kenneth H. Kortright

It is certified that error appears in the above-identified patent and that said Letters Patent is hereby corrected as shown below:

Column 2, line 66, change "HB 8907" to --HB 8709--.

Column 3, line 3, change "side" to --site--.

Column 3, line 23, change "samples" to --sample--.

Column 3, line 58, change "anbibody" to --antibody--.

Column 3, line 63, change "neurominidase" to --neuraminidase--.

Column 4, line 35, change "KC-monoclonal" to --KC-4 monoclonal--.

Signed and Sealed this

Thirteenth Day of September, 1988

Attest:

DONALD J. QUIGG

Attesting Officer    Commissioner of Patents and Trademarks